(12) United States Patent
Kitson

(10) Patent No.: US 7,388,972 B2
(45) Date of Patent: Jun. 17, 2008

(54) ORTHOPAEDIC SURGERY PLANNING

(75) Inventor: David Kitson, Dudsbury (GB)

(73) Assignee: Meridian Technique Limited, Southhampton (GB)

(*) Notice: Subject to any disclaimer, the term of this patent is extended or adjusted under 35 U.S.C. 154(b) by 792 days.

(21) Appl. No.: 10/670,640

(22) Filed: Sep. 24, 2003

(65) Prior Publication Data

US 2005/0054917 A1    Mar. 10, 2005

(51) Int. Cl.
*G06K 9/00* (2006.01)
(52) U.S. Cl. .................................................. 382/128
(58) Field of Classification Search ......... 382/128–132, 382/203, 209, 217, 254, 266; 600/427, 407; 128/920, 898, 922–923; 623/914; 345/629–630, 345/632, 634, 641
See application file for complete search history.

(56) References Cited

U.S. PATENT DOCUMENTS

| | | | |
|---|---|---|---|
| 5,360,446 A | | 11/1994 | Kennedy |
| 5,871,018 A * | | 2/1999 | Delp et al. ................. 128/898 |
| 5,977,979 A * | | 11/1999 | Clough et al. .............. 345/422 |
| 6,002,859 A * | | 12/1999 | DiGioia et al. .............. 703/11 |
| 6,190,320 B1 * | | 2/2001 | Lelong ....................... 600/439 |
| 6,424,332 B1 * | | 7/2002 | Powell ....................... 345/156 |
| 6,533,737 B1 * | | 3/2003 | Brosseau et al. ........... 600/595 |
| 6,584,339 B2 * | | 6/2003 | Galloway et al. .......... 600/426 |
| 6,692,448 B2 * | | 2/2004 | Tanaka et al. .............. 600/587 |
| 6,701,174 B1 * | | 3/2004 | Krause et al. .............. 600/407 |
| 6,711,432 B1 * | | 3/2004 | Krause et al. .............. 600/427 |
| 7,039,225 B2 * | | 5/2006 | Tanaka et al. .............. 382/128 |
| 2002/0059049 A1 | | 5/2002 | Bradbury et al. |
| 2003/0176860 A1 * | | 9/2003 | Shimura ..................... 606/53 |

FOREIGN PATENT DOCUMENTS

| | | |
|---|---|---|
| DE | 43 41 367 C1 | 6/1995 |
| DE | 100 03 533 A1 | 1/2000 |
| EP | 1 188 421 A2 | 3/2002 |
| EP | 1 188 421 A3 | 7/2003 |

(Continued)

OTHER PUBLICATIONS

Fa. Hectec Brochure extracts 1999, 6 pages.

(Continued)

*Primary Examiner*—Andrew W. Johns
*Assistant Examiner*—Andrae Allison
(74) *Attorney, Agent, or Firm*—Courtney Staniford & Gregory LLP

(57) ABSTRACT

A computer-implemented method of planning orthopaedic surgery comprises providing a library of templates representing orthopaedic prostheses, displaying and scaling one or more patient images such as X-ray images, allowing a user to reconfigure geometrical constructs displayed over the images to match the construct to anatomical features shown in the image; and selecting one or more templates from the library in accordance with parameters of the reconfigured constructs. The templates correspond to the orthopaedic prosthesis or prostheses which are most suitable for the patient. Hip replacement surgery can be planned using a single patient image. Knee surgery can be planned using two patient images showing different views of the anatomical features, in which case geometrical constructs for use with each view are provided. The library of templates is accessible via the Internet so as to be accessible by users in any location and readily updateable.

33 Claims, 11 Drawing Sheets

FOREIGN PATENT DOCUMENTS

| | | |
|---|---|---|
| WO | WO 92/00045 | 1/1992 |
| WO | WO 00/41626 | 7/2000 |

OTHER PUBLICATIONS

Fa. Link Brochure extracts, not dated, 8 pages.
Invitation and program of the public statusseminar, 2001, 4 pages.
Juergen Wahrburg, et al., Computer-Assisted Planning for Total Hip Replacement Procedures Based on Multiple 2D Images, CAOS Conference 2001, Pittsburgh Pennsylvania, 3 pages.
Universitat Siegen Brochure, not dated, "Interactive Surgery Robot System", 6 pages.
Siemens brochure "Die Software zur digitalen Operationsplanug und—documentation—EndoMap", allegedly dated 2000 (publication date not clear, and not yet properly verified by the opponent).
English translation of reference listed above.
"Biomechanisch fundierte Huftoperationsplanung mit Hilfe des Softwaremoduls EndoMap", from Electro medica, issue 1, vol. 70, pp. 41-46, Jan. 2002.
"Operations-Planung am PC", from PC-magazine, 23/95, pp. 54-55, May 31, 1995.

* cited by examiner

ORTHOPAEDIC SURGERY PLANNING

RELATED APPLICATION

This application claims priority from United Kingdom Patent Application Number 0222414.5, filed Sep. 26, 2002, which is hereby incorporated by reference in its entirety.

TECHNICAL FIELD

The disclosed embodiments relate to methods and computer program products for planning orthopaedic surgery, in particular surgery for the replacement of hip and knee joints.

BACKGROUND OF THE INVENTION

Orthopaedic surgery includes the replacement of damaged or worn joints with prostheses or implants. It is desirable to perform some pre-operative planning in order to select a prosthesis which is an appropriate size for the patient. Typically, this is done by using templates representing a two-dimensional projection of a three-dimensional prosthesis. The templates are in the form of pre-printed acetate sheets which are overlaid on X-ray images of the joint which is to be replaced. This technique allows a surgeon to choose a suitable prosthesis from those available, and also to plan surgical cut lines and determine the required orientation of the prosthesis. The X-ray image with its overlaid template is referred to by the surgeon during the operation.

However, there are a number of disadvantages associated with this templating technique. In general, it only provides an approximate guide to prosthesis size because X-ray images have a range of magnifications, which for any given image may not correspond with magnifications assumed in available templates. In any case, the exact magnification may not be known. Accuracy may also be compromised by the orientation of bones shown in the image; any bone lying in a plane non-parallel to the image plane will appear foreshortened so that its length and position will be difficult to determine.

Any inaccuracies in the planning process can lead to the selection of an unsuitable prosthesis. This may result in increased length of the subsequent operation, as the surgeon may require an alternative prosthesis to be obtained or may have to make additional or further incisions beyond those planned. In the longer term, a poorly selected prosthesis is more likely to fail early or be subject to other post-operative complications, and require substitution at a later date.

All of these factors tend to increase costs by requiring extra hospital staff time and patient care, and also cause increased pain and inconvenience to the patient.

Consequently, it is desired to provide an improved orthopaedic surgery planning method.

SUMMARY OF THE INVENTION

Accordingly, a first aspect of the present invention is directed to computer-implemented method of planning orthopaedic surgery, comprising:

providing a library of templates representing orthopaedic prostheses;

displaying a patient image showing anatomical features that are relevant for the orthopaedic surgery being planned;

scaling the patient image according to user input;

displaying over the patient image a geometrical construct defined by a plurality of interrelated geometric parameters;

allowing a user to reconfigure the geometrical construct by adjusting the geometric parameters according to the anatomical features of the underlying patient image; and selecting at least one template from the library in accordance with the geometric parameters set by the user.

The benefits of a computer-implemented method of planning orthopaedic surgery are substantial. There is currently a great interest in developing digital medical imaging techniques, including digital radiography. The resulting digital images can be stored in a central archive in a hospital and accessed either from a computer workstation positioned on a local computer network within the hospital or from a more remote machine by making use of the Internet. Also, they can readily and quickly be transferred between hospitals if patients are moved. Such features are advantageous over corresponding ways of working with conventional images such as X-ray films, which exist only as a single version; are costly to produce, time-consuming to transfer, for example via internal and external postal networks; and are prone to loss or damage. Moreover, the images themselves can be of better quality than those obtained by conventional imaging methods, and in the case of radiography, lower X-ray doses can be used, which is clearly beneficial to patient health.

New systems for handling these digital images in ways which derive the most benefit from them have been developed. Most notable at the present time are the Picture Archiving and Communications Systems (PACS) which are being introduced into hospitals. These are systems which can electronically acquire, manage, store and deliver digital images for a whole hospital. Images can be stored directly to a central archive from digital imaging apparatus used to obtain them. Each image is stored together with associated patient information, and can be accessed from any workstation connected to the archive, or possibly remotely over the Internet or a large area network. The patient images may be stored in a variety of file formats, such as .jpeg, .tiff, or .gif. Use of an image format that is compatible with the DICOM standard is preferred, as this is commonly used in hospitals for handling digital images.

With these improved image acquisition and storage methods comes the need to adapt old techniques to the new digital images. In the case of planning orthopaedic implant surgery, if a surgeon desires to use the conventional templating technique, he must produce a hard copy of the relevant digital X-ray image. This is costly, slow and negates many of the advantages of the digital image systems. Conversely, using a computer to perform planning allows many disadvantages of conventional templating to be addressed, so that it may be beneficial in some cases to convert a film X-ray to a digital image to allow computer-implemented planning to be performed.

By handling X-rays digitally and planning procedures on screen, it will be possible to eliminate both the direct cost of films and also indirect costs such as hard-copy management and environmental costs. In the longer term, digital X-ray and planning technology will enable teleradiology applications.

The present invention allows any magnification of the X-ray image to be accurately taken into account and corrected for. This helps to avoid selection and subsequent implantation of an incorrectly sized prosthesis, thus increasing the chance that the operation will be successful.

Also, it is possible to ensure that the surgeon has access to templates of all available prostheses at any given time, by providing the templates in a library, which can be stored on the computer or elsewhere on an associated network. The library can readily be kept up to date and can carry a wide range of templates. Often, a hospital will stock prostheses from only one or two manufacturers, so the library is preferably arranged so only a subset of the included prostheses is accessible by a user in that hospital, corresponding to those used by (and in many cases stocked by) the hospital. Also, the use of digital images in conjunction with digital templates removes difficulties arising from the magnification of the images, such as the need to provide a wide selection of differently sized acetate templates to cover a range of magnifications.

The use of an adjustable geometrical construct introduces a high level of flexibility into the planning method, by allowing the surgeon to fit the construct accurately in all directions. This assists the surgeon to specify a precise mapping of the patient's bone structure, giving a better match to the available prostheses. The geometrical construct may be specific to and customized to a brand of orthopaedic prosthesis previously selected by the user.

In a preferred embodiment the patient image is an X-ray image. Typically, surgeons will use X-ray images to plan orthopaedic surgery. However, the present invention is not limited to the use of X-ray image. The patient image may alternatively by any suitable medical image showing the anatomical features of interest. These may include images obtained by computer tomography or magnetic resonance imaging.

The geometric parameters may include lengths and/or angles. This allows anatomical features to be mapped in a way that corresponds with characteristics of the prostheses.

The method may further comprise, before the selecting:
displaying a further patient image showing anatomical features that are relevant for the orthopaedic surgery being planned;
scaling the further patient image according to user input;
displaying over the further patient image a further geometrical construct defined by a plurality of interrelated further geometric parameters; and
allowing a user to reconfigure the further geometrical construct by adjusting the further geometric parameters according to the anatomical features of the underlying further patient image;
and wherein the selecting at least one template is in accordance with the geometric parameters and the further geometric parameters set by the user.

Some orthopaedic surgical procedures can usefully be planned by considering two alternative images of the anatomical features of interest. Both the prostheses and the bone structure are three-dimensional, so that consideration of the bone structure from more than one view can lead to the choice of a better fitting prosthesis, because geometric parameters in three dimensions can be used in the template selection. For example, the patient image may be an anterior-posterior view and the further patient image can be a medio-lateral image. Alternatively, three or more patient images can be used in the planning method.

In one embodiment, the geometric parameters can be adjusted according to anatomical features of a femur so as to allow selection of a template representing a femoral component of a hip prosthesis and/or a template representing an acetabular component of a hip prosthesis. The method is well-suited to the planning of hip replacement surgery, which can be performed relatively simply using a single X-ray image of the patient's pelvic area, typically in an anterior-posterior view. However, hip revision surgery, in which a failed prosthesis is replaced, may require consideration of two patient images.

In an alternative embodiment, the geometric parameters and further geometric parameters are adjusted according to anatomical features of a knee joint so as to allow selection of templates representing femoral and tibial components of a knee prosthesis. The planning of knee replacement surgery typically requires two orthogonal images of the knee joint to be considered, to provide sufficient parameters for a good match of prosthesis to be obtained.

A second aspect of the present invention is directed to a computer-implemented method of planning orthopaedic surgery, comprising:
providing a library of templates representing orthopaedic implants;
displaying first and second patient images showing anatomical features that are relevant for the orthopaedic surgery being planned;
scaling the first and second patient images according to user input;
displaying over the first patient image a first view of a geometrical construct, the geometrical construct being defined by a plurality of geometric parameters in three dimensions;
displaying over the second patient image a second view of the geometrical construct;
allowing a user to reconfigure the geometrical construct according to the anatomical features of the underlying patient images, by adjusting geometric parameters adjustable in the first and second views; and
selecting a template from the library in accordance with the geometric parameters set by the user.

The method according to the second aspect is well-suited to complex planning, such as for a knee replacement operation. As mentioned above, to obtain a good fit for a knee implant, the surgeon normally considers more than one patient image, taken from different directions, which is laborious when using conventional acetate templates. According to the above-described first aspect of the present invention, two images can readily be considered by providing a geometrical construct for each image, and using the geometrical parameters from each to select the template. The second aspect achieves the same result by the alternative approach of providing a single three-dimensional geometrical construct which is viewed in each image direction as a two-dimensional projection in that direction. The patient's bone structure can hence be mapped in all relevant directions at once, with no mismatch between templating of the two images. This approach permits ready extension of the method to further image directions, because there is no need to provide further individual constructs, merely further projections of the existing construct. The computer-implemented scaling allows both images to be properly scaled, thus eliminating any errors which may arise if the images have different magnifications.

In one embodiment, the first patient image is an anterior-posterior view and the second patient image is a medio-lateral view.

The geometric parameters can be adjusted according to anatomical features of a femur and/or a tibia so as to allow selection of a template representing a femoral component of a knee prosthesis and/or a template representing a tibial component of a knee prosthesis.

Alternatively, the geometric parameters can be adjusted according to anatomical features of a femur so as to allow selection of a template representing a femoral component of a hip prosthesis.

According to a third aspect of the present invention there is provided a computer program product carrying machine-readable instructions for implementing the method of the first aspect of the invention. According to a fourth aspect of the present invention there is provided a computer program product carrying machine-readable instructions for implementing the method of the second aspect of the invention. The machine-readable instructions may be stored in a recording medium, such as volatile or non-volatile computer memory, magnetic or optical storage media. The machine-readable instructions may also be conveyed on a transmission medium, such as a wireless transmission medium, a conducting cable or an optical cable.

According to a fifth aspect of the present invention there is provided a computer system for implementing a method of planning orthopaedic surgery, comprising:

memory in which is stored:
a library of templates representing orthopaedic prostheses; and
patient images showing anatomical features that are relevant for the orthopaedic surgery being planned;
a display device operable to display one of the patient images; and
a processor operable to:
scale the displayed patient image according to user input;
display over the patient image a geometrical construct defined by a plurality of interrelated geometric parameters;
allow a user to reconfigure the geometrical construct by adjusting the geometric parameters according to the anatomical features of the displayed patient image; and
select at least one template from the library in accordance with the geometric parameters set by the user.

In one embodiment, the display device is further operable to display a further one of the patient images; and
the processor is further operable to:
scale the displayed further patient image according to user input;
display over the further patient image a further geometrical construct defined by a plurality of interrelated further geometric parameters;
allow a user to reconfigure the further geometrical construct by adjusting the further geometric parameters according to the anatomical features of the displayed further patient image; and
select at least one template from the library in accordance with the geometric parameters and the further geometric parameters set by the user.

According to a sixth aspect of the present invention there is provided a computer system for implementing a method of planning orthopaedic surgery, comprising:

memory in which is stored:
a library of templates representing orthopaedic prostheses; and
patient images showing anatomical features that are relevant for the orthopaedic surgery being planned;
a display device operable to display a first and a second of the patient images; and
a processor operable to:
scale the displayed patient images according to user input;
display over the first patient image a first view of a geometrical construct, the geometrical construct being defined by a plurality of geometric parameters interrelated in three dimensions;
display over the second patient image a second view of the geometrical construct;
allow a user to reconfigure the geometrical construct according to the anatomical features of the underlying patient images, by adjusting geometric parameters adjustable in the first and second views; and
select a template from the library in accordance with the geometric parameters set by the user.

In a preferred embodiment, the library of templates is stored such that it can be accessed by the processor via the Internet. This arrangement gives a central library that can be administered by a single provider and accessed by users in any hospital with Internet access. In this way, library can conveniently be kept fully up to date for all users.

Advantageously, the patient images are stored in an archive comprised within a Picture Archiving and Communication System.

BRIEF DESCRIPTION OF THE DRAWINGS

For a better understanding of the invention and to show how the same may be carried into effect reference is now made by way of example to the accompanying drawings in which.

DETAILED DESCRIPTION

First Embodiment—Hip Replacement Surgery Planning

The first embodiment of the invention relates to computer-implemented planning for hip replacement surgery. In this operation, the head of the femur is replaced with a metal implant having a stem which is inserted into the canal within the femur (femoral component), and/or the acetabulum in the pelvis is replaced with a metal, ceramic or plastic cup-shaped implant (acetabular component). In this example, the planning is based on a previously obtained X-ray image of a patient's pelvic region, although images obtained by alternative imaging techniques may also be used.

Figure 1:
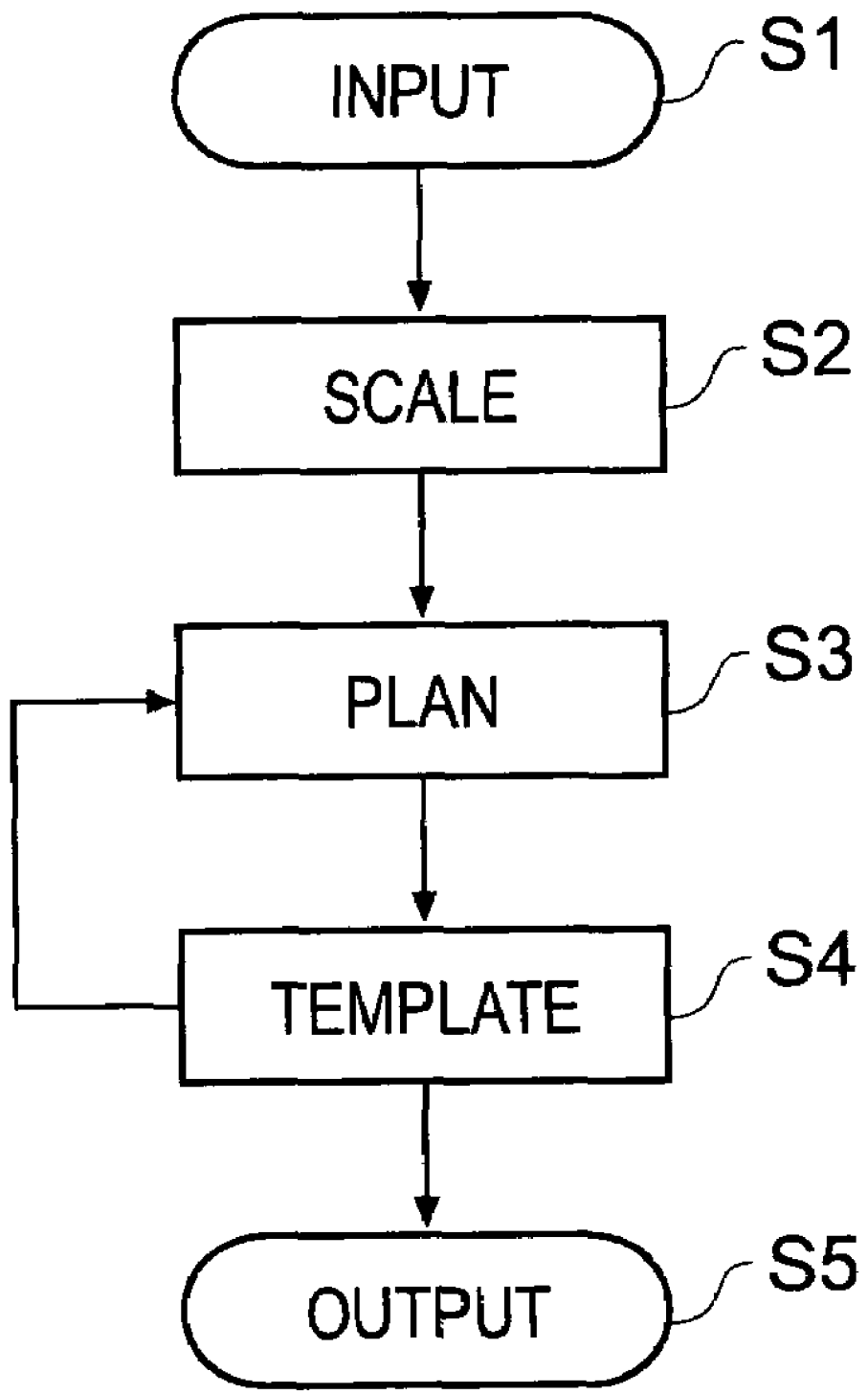
FIG. 1 is a flow diagram illustrating steps in a method of planning orthopaedic surgery according to embodiments of the present invention.

FIG. 1 shows the basic steps of the planning procedure.

In Step S1, an input step, an X-ray image is loaded into a computer system and displayed to a user. The computer system contains software operable to execute the various steps of the planning procedure. The X-ray image is an anterior-posterior (from the front) view of the patient showing anatomical features that are relevant for the hip replacement surgery being planned, namely the pelvis and upper parts of the left and right femurs.

In Step S2, a scaling step, the X-ray image is scaled according to user input so that dimensions of the relevant bones can be accurately compared with assorted sizes of prosthesis. The scaling step is performed in a scaling window displayed by the computer system.

In Step S3, a planning step, a geometrical construct defined by a plurality of interrelated geometric parameters is displayed over the X-ray image. The user configures the geometrical construct by adjusting its geometric parameters according to the anatomical features of the underlying pelvic image. The planning step is performed in a planning window displayed to the user by the computer system.

In Step S4, a templating step, templates of the prosthetic components are displayed over the X-ray image. The templates are scaled representations of femoral and acetabular components that have been selected automatically according to a prosthesis selection algorithm. This algorithm selects the templates from a template library or database in accordance with the geometric parameters set by the user in the planning step. The templating step is performed in a templating window displayed to the user by the computer system. There is also the facility to allow the user to return to the planning window from the templating window and readjust the geometrical construct, for example if the displayed template represents an apparently unsatisfactory prosthesis. The prosthesis selection algorithm can then be reapplied to update the templating window. This iterative possibility is indicated by the feedback arrow leading from Step S4 to Step S3 in FIG. 1. It is also possible for the user to position and rotate the template directly.

In Step S5, an output step, the surgery planning is complete and the result of the planning procedure is output from the computer system. The result is the specification of a prosthesis from those determined by the prosthesis selection algorithm as being suitable for the patient.

Each of the steps is now discussed in more detail.

Step S1—Input

The input step involves obtaining a digital version of the desired X-ray image and displaying it on a workstation for viewing by the user. Preferably, the workstation has access to a Picture Archiving and Communication System (PACS). This is a hospital-based computerised system which can store diagnostic images of different types (including X-ray images, computerised tomography (CT) images, magnetic resonance imaging (MRI) images) in a digital format organised in a single central archive. Each image has associated patient information such as the name and date of birth of the patient also stored in the archive. The archive is connected to a computer network provided with a number of workstations, so that users all around the hospital site can access and view any image as needed. Additionally, users remote from the site may be permitted to access the archive over the Internet.

If a PACS archive is available, the input step is achieved by the user accessing the PACS archive and selecting the appropriate X-ray image. The data file for the image is then transferred over the network to the user's workstation, and the image is displayed on the workstation's monitor.

In the absence of a PACS or similar archive, the digital X-ray image may be provided on a CD-ROM or other computer readable storage device, or downloaded directly from a digital radiography imager, which takes X-ray images in a digital format. If it is desired to use an X-ray image which has been recorded on film in the conventional manner, it will be necessary to convert the film image to a digital image file using a film digitiser. The digital image can then be stored on a computer readable storage device or entered onto a PACS archive, for future access.

It is also necessary during the input step to set up access to a library or database containing details of all the available prostheses, and therefore the procedures that may be planned. The database may be located on the workstation on which the user is performing the planning, or it may be on a separate computer system connected to the workstation via a computer network, such as a local area network, or via the Internet. The database may be downloaded and/or updated from a remote location to the workstation via such a network. The database may be updated by adding or removing data. It is important that the database be kept up to date, so that the planning process does not result in the selection of a template which no longer accurately represents the corresponding prosthesis or which contains labelling or other information that no longer correctly reflects the corresponding prosthesis or which has been withdrawn by the manufacturer. Templates may be provided with expiration dates to facilitate this. Depending on how the database is administered, it may therefore be necessary to set up a link to the database at the start of each planning session, to ensure that the most up-to-date version of the database is used. To simplify the provision of the database to users in different hospitals, the database is advantageously compiled, administered and updated by an external provider. The database contains details of all prostheses currently on the market, and is adapted for use in individual hospitals by being configured so that a user can only access details of prostheses actually stocked by the relevant hospital. Each hospital can be supplied with one or more copies of the database. In a preferred embodiment, however, a single central database is made available and maintained by the external provider and accessed by the user over the Internet. Access to templates may thereby be restricted to legitimate users.

Figure 1A:
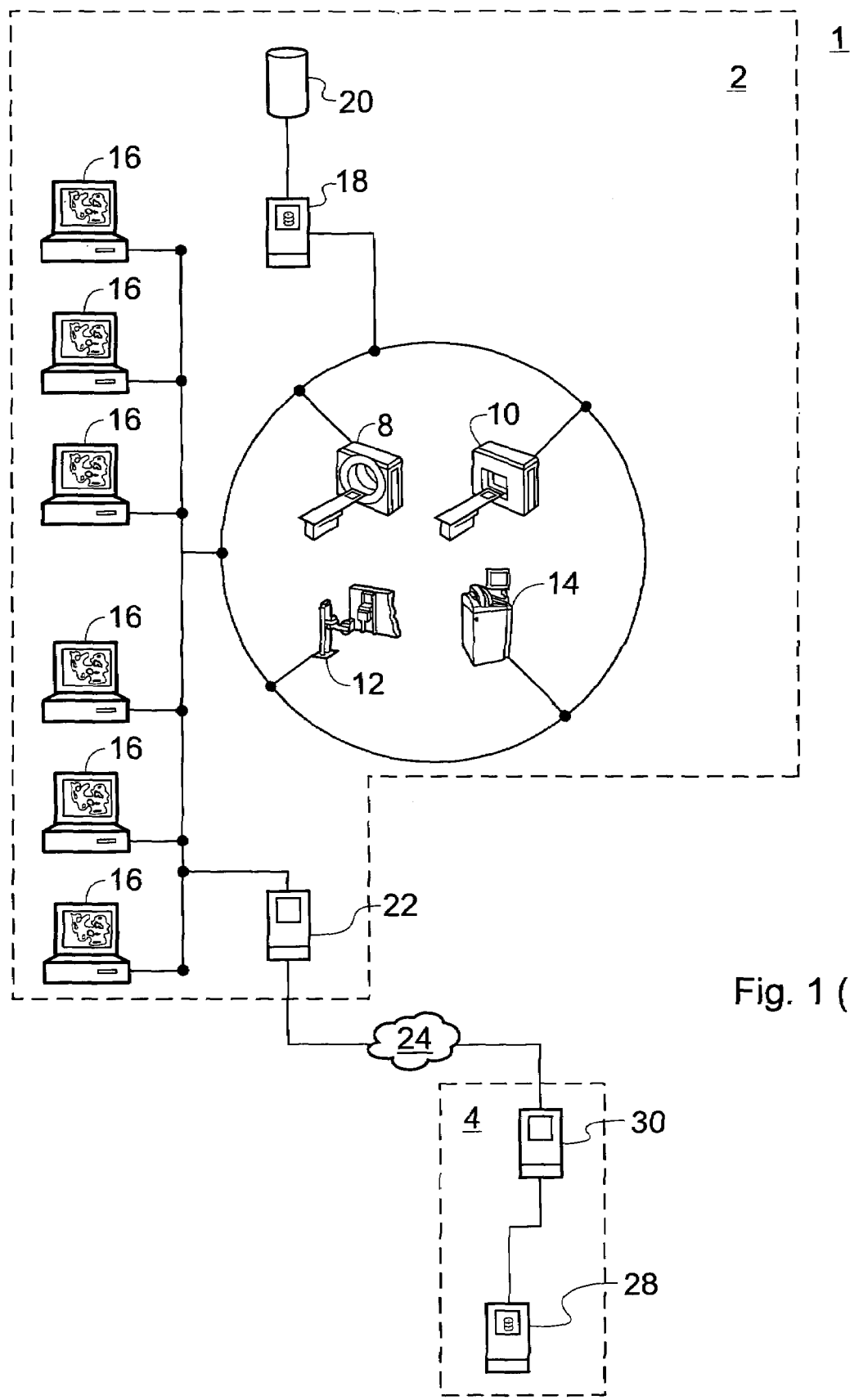
FIG. 1(a) shows a schematic diagram of a computer network suitable for implementing the method of FIG. 1.

FIG. 1(a) shows an example computer network which can be used to implement an embodiment of the method of the present invention. The network 1 comprises a local area network in a hospital 2. The hospital 2 is equipped with a number of workstations 16 which each have access, via the local area network, to a hospital computer server 18 having an associated storage device 20. A PACS archive is stored on the storage device 20 so that images in the archive can be viewed at any of the workstations 16. Also, a number of medical imaging devices 8, 10, 12, 14 are connected to the hospital computer server 18. Images recorded with the devices 8, 10, 12, 14 can be stored directly into the PACS archive on the storage device 20. The local area network is connected to the Internet 24 by a hospital Internet server 22. An external database provider 4 maintains a database of prostheses for use in the method of the present invention. The database is stored on a provider server 28, which is connected to the Internet 24 by an Internet provider server 30. Hence workstation users in the hospital 2 can access the database of prostheses via the Internet 24.

The database includes an entry, or data file, for each available separable component of a prosthesis which could be chosen for use as a result of using the planning method. In the present embodiment, there are a series of data files for femoral components and a series for acetabular components. The data file is implemented as an object. Various fields are provided for each data file, so that all the information which is needed for selection of the most appropriate prosthesis is available. This typically includes a wide range of measurements and angles describing the shape of the prosthetic component, its intended relationships to the bones, and possibly the materials from which the prosthesis is made. Additionally, each entry should include user-friendly information which uniquely identifies each prosthesis (for example by manufacturer name and serial number) and is comprehensible when returned to the user at the end of planning, to allow procurement of the required prosthesis. Also, an alternative identifier may be included, such as a unique code number, for internal computer network use, for example, communication with a stock control program.

Each data file in the database is structured so as to have a header part, containing prosthetic system identification data, and a body part containing two-subdivisions. A prosthestic system includes the prosthesis components and may include other material such as measuring devices, and represents a particular product range from a manufacturer. Each prosthetic system may be embodied in a single data file in the database. One subdivision of the body part contains field definitions defining the relevant characteristics of the prosthesis (such as "femoral size", "offset angle"), and the other subdivision contains records or values for each field definition. The data file may also contain graphical banners for display to the user, and an expiration date. The data file also contains data relating to the X-ray view and patient side (left/right) for which the data file is appropriate.

Finally, before the remainder of the planning procedure can be undertaken the user is required to enter information relating to the planning which is going to be performed. In particular, details of whether the operation is to be performed on the right or left side of the patient's body, and the type of operation being planned, i.e. what prosthesis is to be implanted, is required. This enables appropriate geometrical constructs and templates to be displayed during the planning procedure. Also, the user is required to indicate a range of prostheses which are to be considered during planning, for example, prostheses or prosthetic systems from a particular manufacturer. This facility is provided because many surgeons prefer to work with only one or two brands of prosthesis, so it is advantageous to limit the range appropriately before planning begins. All this information is entered using a standard data information box displayed on the screen, which prompts the user for the necessary data.

Step S2—Scaling

Once the X-ray image is displayed, it is scaled or calibrated in a scaling step, so that the physical dimensions of the patient's bone structure can be determined and used to choose an appropriately sized prosthesis.

The bones shown in X-ray images contain a degree of magnification, which may or may not be known. This arises from the fact that the beam of X-rays used to record the image is not collimated, and is passing through a patient with a given thickness so that the bones themselves are never in direct contact with the imaging surface. If the exact distances between the imaging surface, the bones and the X-ray source are not known, the degree of magnification will also be unknown. To allow scaling in the case where the magnification is not known, the X-ray image should include a reference object of known size in the correct plane, i.e. the plane of the hip joint. The reference object can be any convenient feature that is opaque to X-rays and which has a precisely known size. For example, a precisely machined disc of metal or other reference marker may have been placed in the X-ray field of view in the correct plane at the time the X-ray image was taken. Alternatively, the femoral head of a hip replacement already performed on the same patient can be used as the reference object, if the specification of the femoral component is known.

Scaling is performed using a display window called the scaling window, which displays the X-ray image together with controls to allow the user to implement the scaling step.

Figure 2:
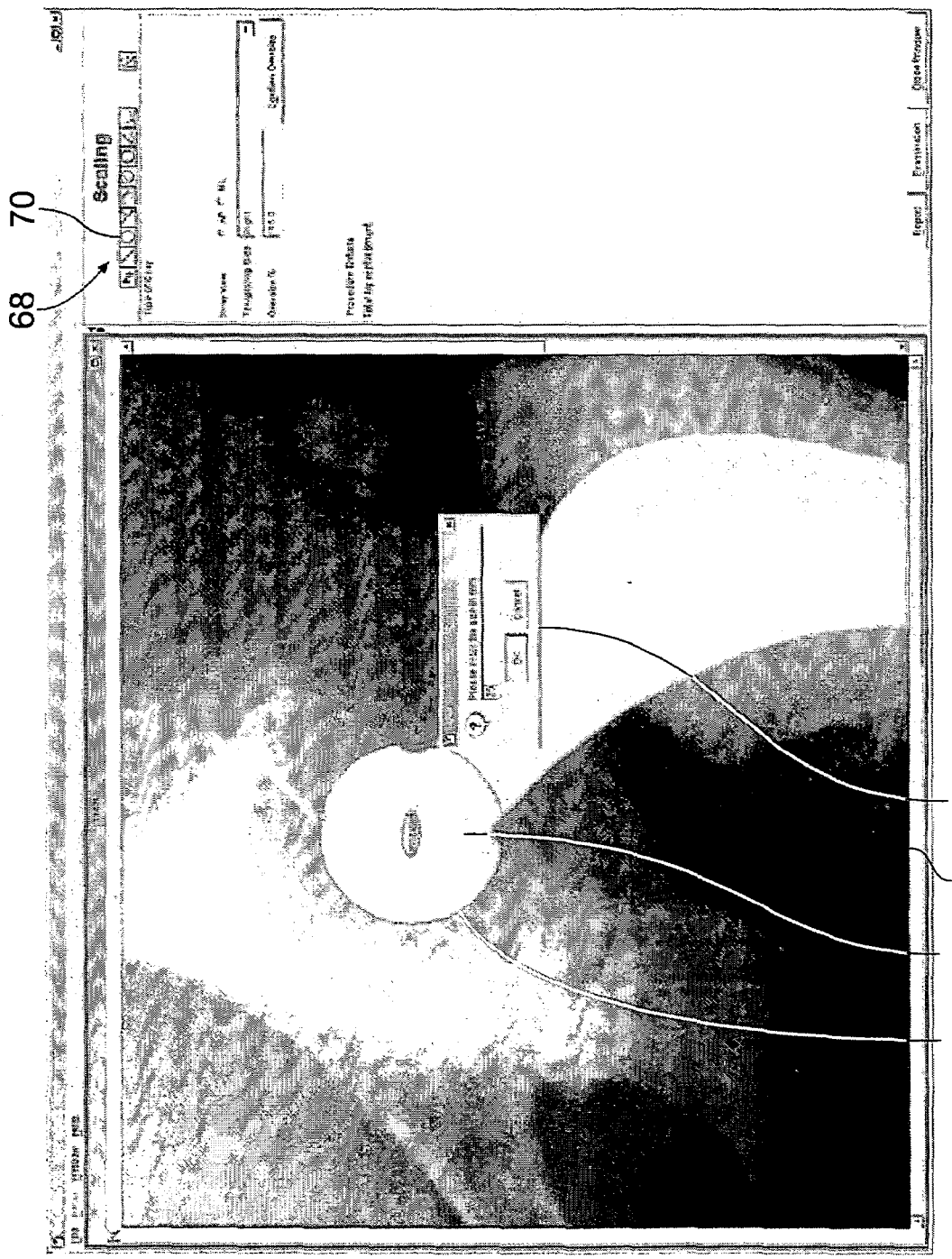
FIG. 2 shows a screen shot of a computer window for performing a scaling step of a first embodiment of the method of FIG. 1.

FIG. 2 is a computer screen shot of the scaling window. In the X-ray image shown 72, the reference object is a previously implanted hip prosthesis with a spherical femoral head 67. To perform the scaling, the user selects one of several scaling tools from a tool bar 68. The tool displays an adjustable shape 66 over the X-ray image 72, which can be manipulated by the user (using a mouse or other computer input device) to match the size and shape of the X-ray opaque object. In this case, the user has selected a tool 70 which gives a circular shape 66. Once the user has correctly positioned and sized the circular shape 66 on the X-ray image 72, the user opens a data entry box 76. The user then types the actual known size of the opaque object into the data entry box 76, in this case, the diameter of the spherical femoral head 67. This information is used to scale the image 72 appropriately, so that any dimension subsequently defined with reference to the image can be calculated.

Other scaling tools include a linear measure which can be positioned along a known width or length of the opaque object, and a rectangle shape which can be used to outline a rectangular opaque object. Other shapes may be provided as appropriate.

If no suitable opaque object was included in the X-ray image, the magnification must be estimated by the user using knowledge of the protocol used in the hospital radiology department when capturing the image. However, this technique is less accurate and more error-prone than using an opaque object for scaling the image. Alternatively, the magnification of the X-ray image may be known, so that it is not necessary to use one of the adjustable scaling tools from the toolbar 68, or to estimate the magnification. In the case of estimated or known magnification, the user can enter the magnification as a percentage figure into a data entry box (not shown), and this information is used to scale the image. A percentage value of 100 can be entered if the input image is already scaled.

To ensure the accuracy of the planning, the user is required to confirm that the information provided for scaling (size or percentage) is correct before the remainder of the planning procedure can be performed.

Step S3—Planning

Figure 3:
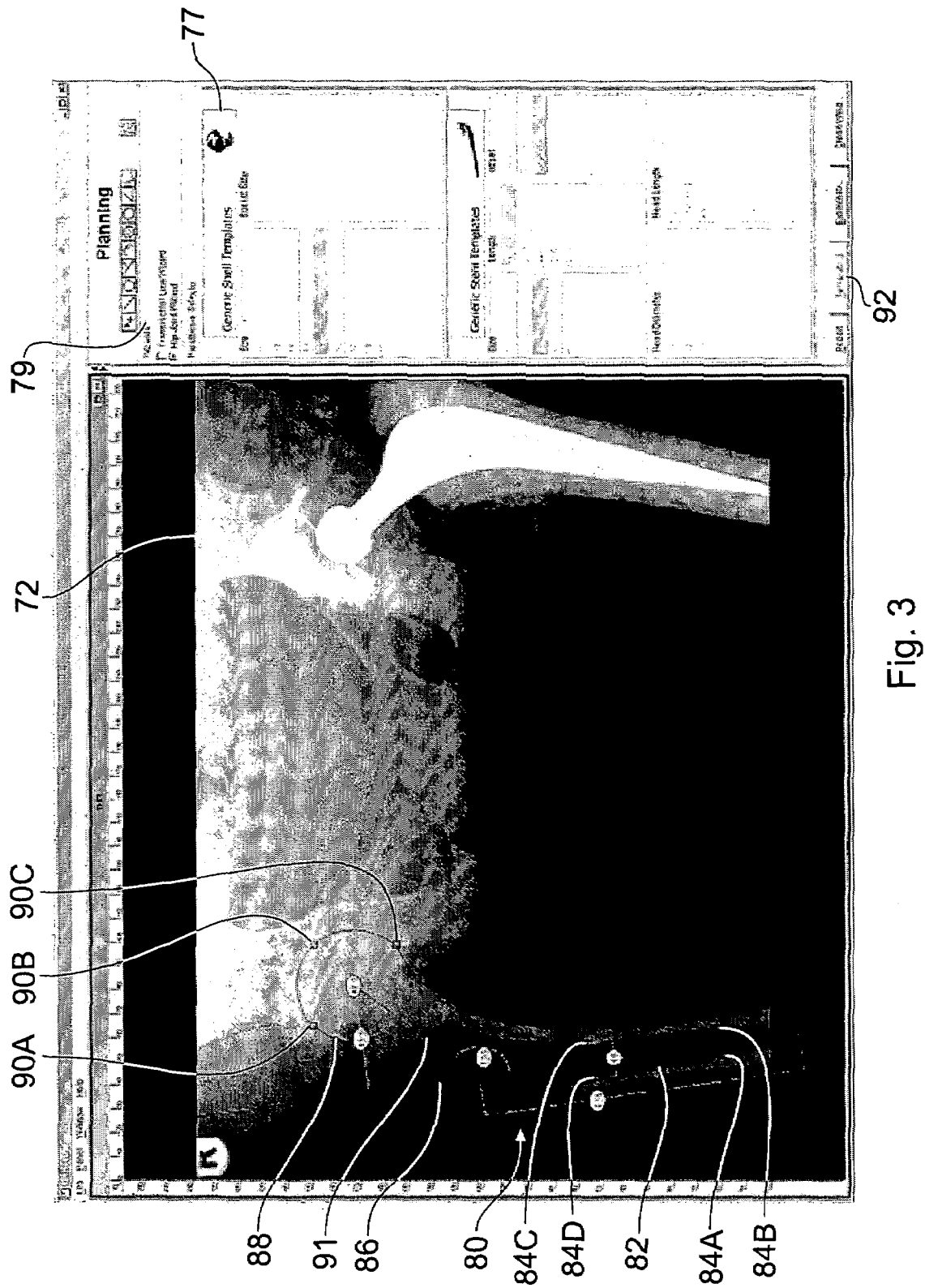
FIG. 3 shows a screen shot of a computer window for performing a planning step of a first embodiment of the method of FIG. 1.

FIG. 3 shows a screen shot of a planning window which is displayed to the user once scaling is complete. The planning window includes the X-ray image 72, a user choice panel 79 for user choice of different planning tools, and information panels 77 showing details of prostheses in available prosthetic systems. Banners showing the available prostheses may be displayed to the user in the information panel 77. The user may select alternative prosthetic systems at this stage.

The user selects from the user choice panel 79 a planning tool corresponding to the operation being planned. In the present example, therefore, a planning tool for planning a hip replacement operation has been chosen.

The planning tool overlays a geometrical construct 80 on the X-ray image 72. The geometrical construct 80 comprises a plurality of shapes and lines which are defined by geometric parameters corresponding to spatial information which is required to select suitable templates. If the geometrical construct is correctly positioned over the X-ray image, the dimensions and layout of the patient's bone structure can be calculated from the size of the construct and the known scale of the X-ray image.

Figure 3A:
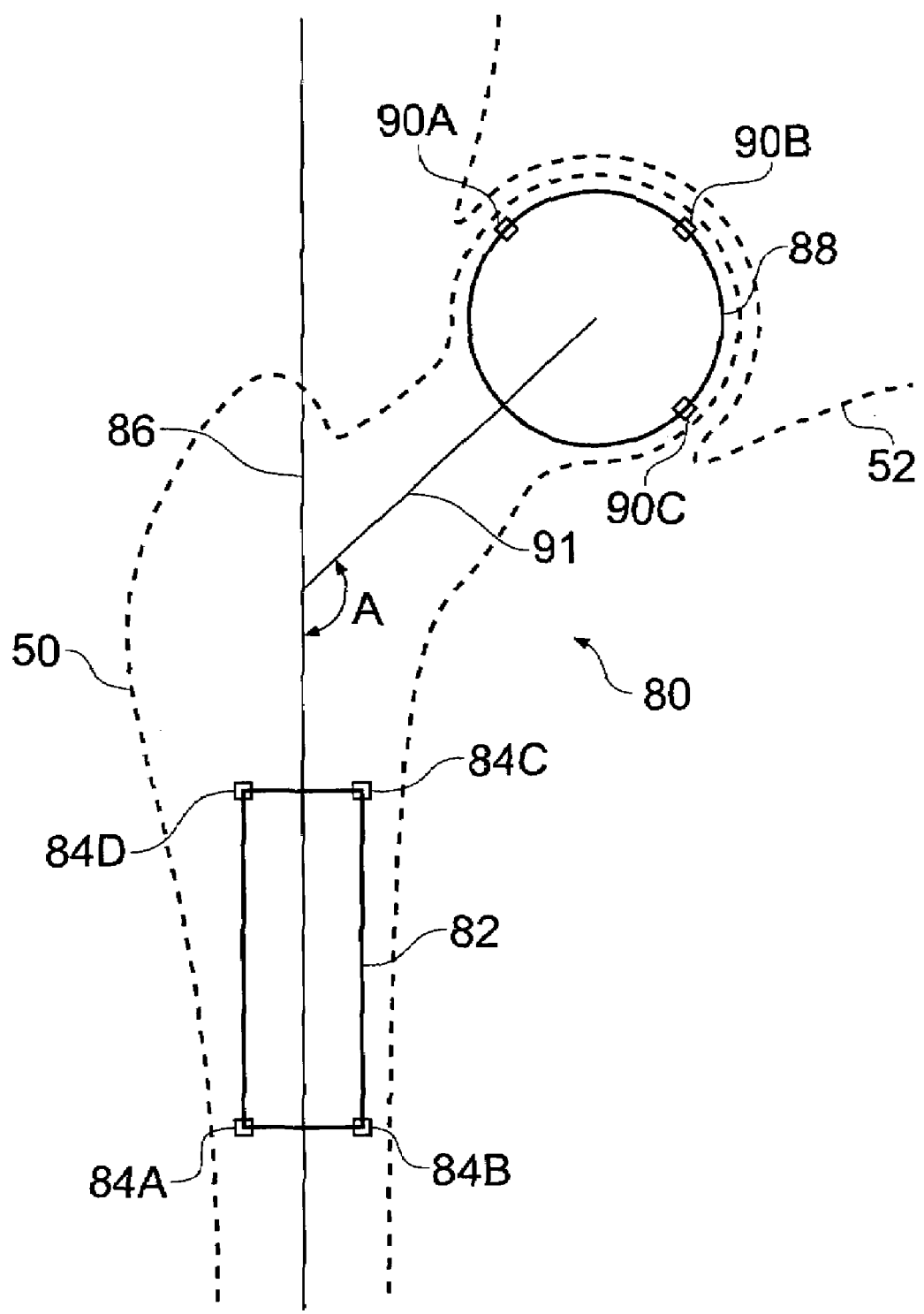
FIG. 3(a) shows a schematic representation of a geometrical construct used in the planning step of FIG. 3.

FIG. 3(a) shows the geometrical construct 80 in more detail. Using common computer parlance, various geometrical constructs described herein will be referred to as "wizards". In the present example, the geometrical construct is therefore termed the hip wizard, and the example shown in FIGS. 3 and 3(a) corresponds to a right hip joint. A femur 50 and an acetabulum 52 are shown in outline in FIG. 3(a), with the wizard 80 overlaid in an approximate position.

The hip wizard 80 comprises a circle 88 having three manipulation handles 90A, 90B and 90C. The centre of the circle 88 is connected by a first line 91 to a second line 86, the first line 91 meeting the second line 86 at fixed angle A, which corresponds to a characteristic angle in the range of prostheses indicated for consideration in the input step S1. The second line 86 has an associated box 82 in the shape of a quadrangle and having a manipulation handle 84A, 84B, 84C and 84D at each corner. The box 82 overlies the second line 86 such that the second line 86 bisects the lines forming short edges of the box 82 between manipulation handles 84A and 84B, and between 84C and 84D.

After the user selects the wizard 80 from the user choice panel 79, the wizard 80 is displayed over the X-ray image 72. The wizard 80 is automatically positioned vertically and horizontally in an initial position which is close to the correct position. This is achieved using prior knowledge and experience of the typical field of view of an X-ray of the pelvic area taken for the purpose of planning hip replacement surgery. The user can drag the hip wizard 80 across the image 72 and resize it by use of the manipulation handles, by using a mouse or similar device. Firstly, the user manipulates the box 82 by dragging each of the corner handles 84A-D so that the box 82 outlines the femoral canal, within the femur. The purpose of positioning the box 82 is to locate the second line 86 (which moves with the box 82 such that it always bisects the box edges 84A-84B and 84C-84D) correctly along the length of the femur such that it follows the longitudinal axis of the bone. This is achieved by positioning the upper part of the box 82 at the point at which the femur is flared, and the lower end of the box far enough down the canal so that the second line 86 is satisfactorily aligned with the axis of the femur.

The user then drags the circle 88 over the femoral head and manipulates the position and size of the circle 88 using the handles 90A, 90B and 90C so that the circle 88 outlines the femoral head.

Each time the wizard 80 or part thereof is repositioned or resized, a selection algorithm is executed, which selects from the database one or more data files representing suitable prostheses. Using the scaling of the image, geometrical parameters are taken from the manipulated wizard 80. Each of these geometrical parameters corresponds to parameters which describe the available prostheses. For example, the length of long edge 84A-84D of the box 82 corresponds to the shaft size (length) of the prosthesis to be implanted; the size of the circle 88 corresponds to the size of the acetabular component; and the distance between the line 86 and the centre of the circle 88 is used to measure the patient's physiological offset (shortest distance between the axis of rotation of the femoral head and the axis of the femoral shaft) and corresponds to the offset size of the prosthesis. Each prosthesis has an associated representative to-scale template which shows a two-dimensional outline of the prosthesis. The parameters of the prostheses are stored in the database linked in the input step. Each prosthesis has a data file which holds pertinent details relating to it, including all relevant dimensions, and manufacturer's details and part numbers, plus data representing the corresponding template.

The selection algorithm compares each of the wizard geometrical parameters in turn with the equivalent parameter for each of the accessible data files representing prosthetic components in the database, and selects one or more prosthetic components which best match the wizard parameters. The algorithm may include specified tolerance levels for particular parameters, so that it can return a range of prostheses of varying suitability. For example, it may be that the particular patient dimensions mean that one prosthesis is a good fit in the femoral component and less good in the acetabular component whereas an alternative prosthesis is a good fit in the acetabular component but less good in the femoral component. The use of tolerances means that the algorithm will identify both prostheses.

Details of the prostheses selected by the selection algorithm are shown to the user in the information panels 77. The panels include lists of a range of values of each prosthesis parameter. The parameter values of the prostheses selected by the selection algorithm are highlighted in the lists, for example by shading of the text. Further manipulation of the wizard 80 causes re-execution of the selection algorithm, and the information panels 77 are then updated to indicate the results of this re-execution. In this way, the user can monitor the selection process and is provided with an immediate visual indication of how any given manipulation of the wizard 80 affects prosthesis selection.

Once the user is satisfied that the position of the wizard 80 correctly reflects the anatomical features of the patient, the user can then click on an on-screen control button 92 to progress to the templating step of the planning procedure.

Step S4—Templating

Figure 4:
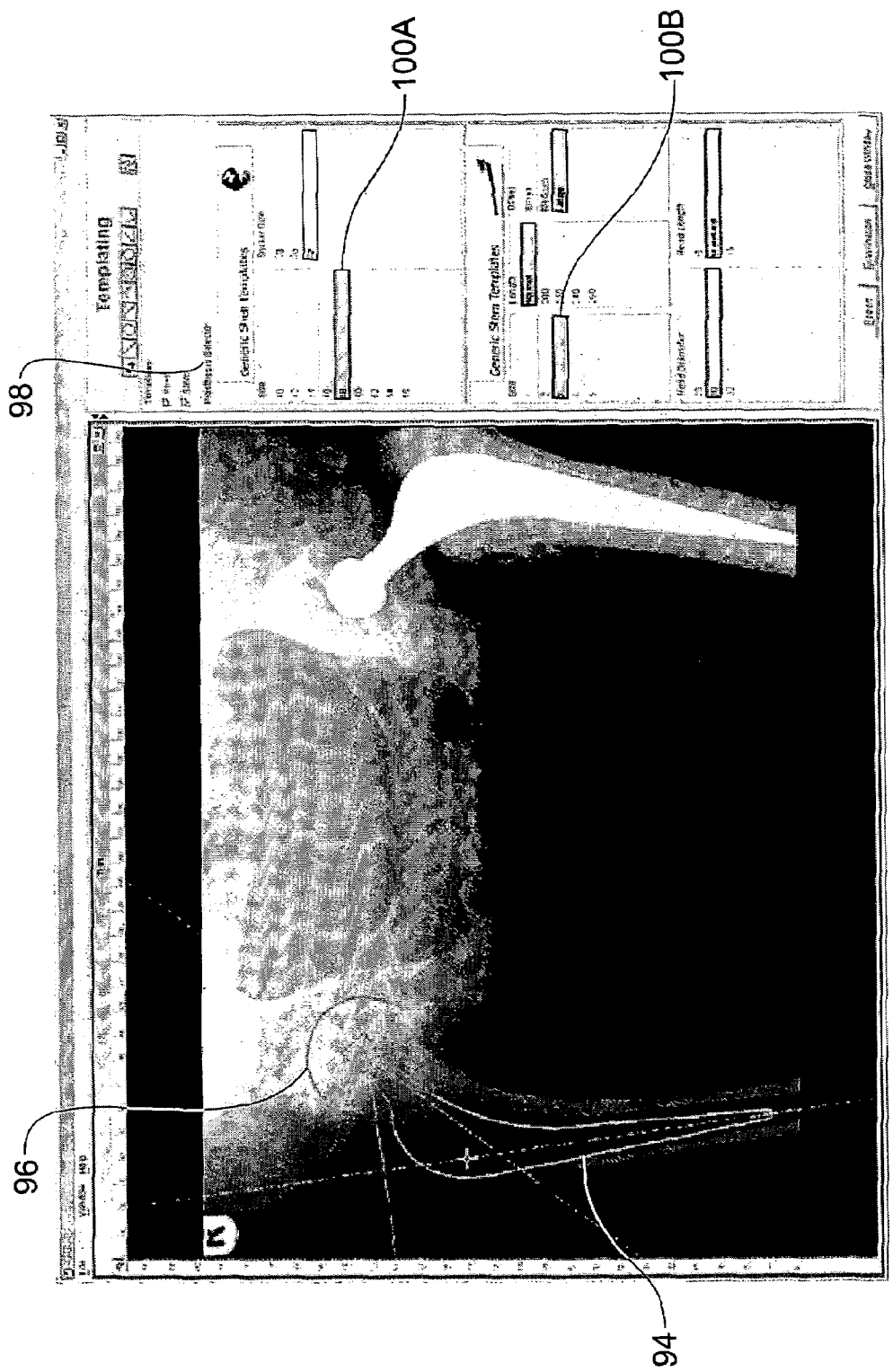
FIG. 4 shows a screen shot of a computer window for performing a templating step of a first embodiment of the method of FIG. 1.

FIG. 4 shows a screen shot of a templating window which is displayed to the user in the templating step. The X-ray image 72 is shown, upon which a template of a prosthesis is superimposed.

The templating window includes a series of prosthesis chooser panels 98, which are similar to the information panels 77 of the planning window, in that the prosthesis chooser panels 98 list a range of values for each prosthesis parameter. The prostheses selected by the selection algorithm in the planning step are presented in the chooser panels 98 as a series of recommendations, identified by shaded areas 100A and 100B overlying the relevant values. Darker shading indicates the best available match for that parameter, while paler shading indicates less good matches which nonetheless fall within the algorithm tolerance levels and are hence regarded as usable. Unshaded values are not recommended for use but may still be chosen by the user using clinical judgement. The user then picks (using a mouse or similar) one parameter from each prosthesis chooser panel 98, using the shaded areas 100A and 100B as an aid to making a suitable choice. Once the user has chosen sufficient parameters from the chooser panels 98 to uniquely identify a particular prosthesis, the template data from the relevant data file and the orientation of the hip wizard from the planning step are used to depict the corresponding template in position over the femur and pelvis in the X-ray image 72. The template consists of outlined parts representing the femoral component of the prosthesis 94, also known as a stem, and the acetabular component 96, also known as an acetabular cup. If an insufficient number of parameters is picked, there will not be enough information to uniquely identify an appropriate data file so that two or more data files may be found to match the user's chosen parameters. In this case, no template is displayed and the user informed via a dialogue box. If no appropriate data file can be found at all, owing to an ill-assorted choice of parameters, again no template is displayed, and the user similarly informed.

The user can then consider the template and make a decision as to whether the prosthesis it represents appears to be suitable, based on how well the template aligns with the patient's bone structure as shown on the X-ray image 72. The user can make alternative choices from the chooser panels 98, to display other templates for the purposes of comparison. The template femoral and acetabular components 94 and 96 may be repositioned by clicking and dragging, to aid in the decision making process.

If the user finds that none of the templates recommended in the chooser panels 98 are a satisfactory match with the patient's bone structure, the user can return to the planning window by clicking on a control included in the template window. The hip wizard can then be further manipulated, and the selection algorithm will be re-executed using the new wizard parameters, with the results shown in the information panels 77. When the user subsequently moves back to the templating window, the shaded values in the chooser panels 98 are updated accordingly to show the modified recommendations as selected by the selection algorithm. Choice of prostheses and display of corresponding templates then continues as before.

To aid in the choice of a suitable prosthesis, the values in the chooser panels 98 lists are displayed in bold or standard text. Standard text is used to represent values which are not available in conjunction with already chosen values of other parameters, owing to the range of prostheses available. The use of standard or bold text is therefore updated each time a value is selected.

Step S5—Output

Once the user has decided on a particular template, and hence also on its corresponding prosthesis, he indicates his choice by clicking on a suitably-labelled button in the template window or menu item (not shown). This action triggers the final step of the planning process, which is the output step.

A record of the choice of prosthesis can be output in one or more ways, depending on the system to which the workstation is connected. A window with checkboxes can be provided on the display for the user to indicate which outputs are required at that time.

Preferably, the output step generates an output data file which records the choice of prosthesis together with the patient's details. The prosthesis will typically be identified by manufacturer name and a serial number, although a particular hospital could use an internal identification system. Additional information can usefully be included in the output data file, such as user's (surgeon's) name, date of planning, and proposed or actual date of operation.

The output step then delivers the output data file in the way indicated by the user or according to pre-set configurations. If the workstation is connected to a PACS archive, the file should be recorded in the archive, with a link to the relevant X-ray image so that the two files can be retrieved together if necessary. Alternatively or additionally, the file can be stored in a separate archive or database unconnected with the X-ray image file which may be on the hard disk of the workstation used or on an alternative data storage medium, or it may be transferred to a different computer, for example, by email. If the workstation is connected to a printer, either locally or over a network, the data file can be printed out as a hard copy for inclusion in the patient's paper records or for use as a memo to other hospital staff.

Additionally, the data file may usefully be sent over a network to a stock control department of the hospital where it can be compared, either manually, or preferably by computer, with records of existing prosthesis stock. In this way, a particular prosthesis can be earmarked for a particular operation, or a stock order can be generated if the prosthesis is not in stock.

Second Embodiment—Knee Replacement Surgery Planning

The second embodiment of the invention relates to computer-implemented planning for knee replacement surgery. In such surgery, the knee capsule is opened, and the ends of the femur and tibia are trimmed and augmented with implants which may or may not be held in place with cement. The femoral component is a metal shell, and the tibial component is a metal and plastic trough.

This embodiment has the same basic steps as the first embodiment, and the planning procedure is performed in a similar way. The two embodiments differ in that the knee replacement planning is usually based on two previously obtained X-ray images of a patient's knee, one from the side (medio-lateral (ML) view) and one from the front (anterior-posterior (AP) view). Unlike the hip, where enough information can usually be derived from a single AP X-ray image, two different views of the knee are used to ensure that the selected prosthesis is a sufficiently good fit. The ML view is normally used to select and choose the femoral component, and the AP view is normally used to select and choose the tibial component.

The images are input and scaled as described above with reference to steps 1 and 2 of the hip replacement planning embodiment. Once the two X-ray images are available and scaled, a planning window is displayed, which includes a view of one of the X-ray images, and a planning tool selector to permit selection of a geometrical construct, or wizard.

Because the knee prosthesis consists of two unconnected parts (the femoral and tibial components), the planning is performed in each of the X-ray image views by using two geometrical constructs or wizards which are independently manipulatable. These are referred to as the femoral wizard and the tibial wizard and respectively correspond to the femoral component and the tibial component of the prosthesis. In the following description, the wizards are referred to with reference to the ML and AP views. Within each view, the femoral and tibial wizards are independent of one another. However, the femoral wizard in the ML view is interrelated with the femoral wizard in the AP view, and similarly for the tibial wizard in each of the two views. The nature of this inter-relation will be discussed in more detail later.

Figure 5:
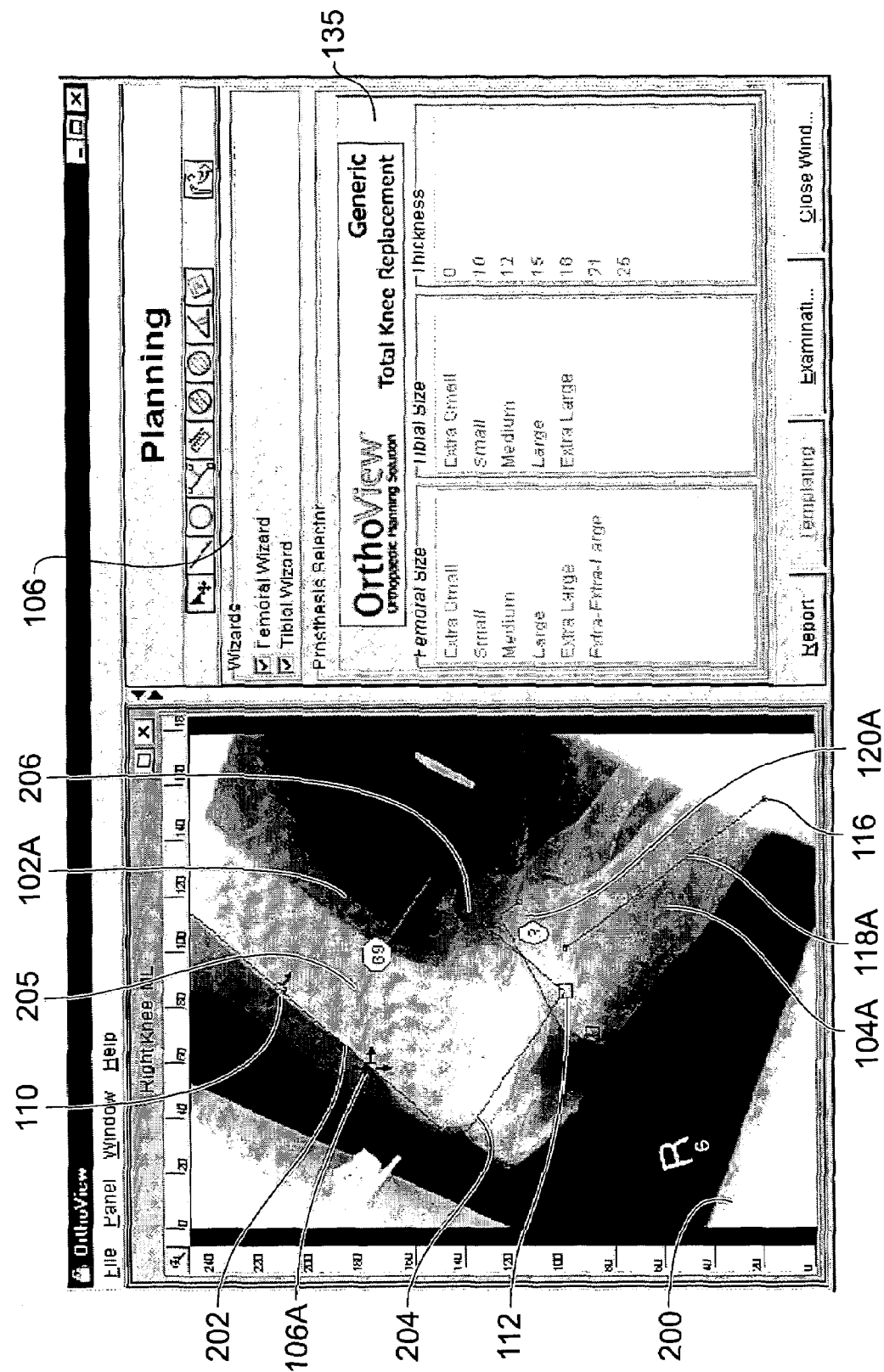
FIG. 5 shows a screen shot of a computer window for performing a planning step of a second embodiment of the method of FIG. 1.

FIG. 5 shows a screen shot of the planning window, with a ML X-ray image 200 displayed. Both the femoral wizard and the tibial wizard have been selected using a planning tool 106, so that the ML view femoral wizard 102A and the ML view tibial wizard 104A displayed overlaid on the knee bones in the X-ray image 200.

FIG. 5(*a*) shows the ML view femoral and tibial wizards 102A, 104A in more detail. An underlying image of a femur 54 and tibia 56 is shown in outline, with the wizards 102A, 104A in an approximate position. The ML view femoral wizard 102A comprises five straight lines. Four of these lines 202, 204, 205, and 206 are connected to form a quadrangular box, with the line 202 extending beyond the box. The fifth line 203 extends across the box parallel to the line 204. The relative lengths of the lines and the angles between them can be altered by dragging on suitably provided drag handles 106, 110 and 112.

The ML view femoral wizard 102A is positioned by using the handle 106 to move the whole wizard 102A so that the extending line 202 is placed on the anterior edge of the femur. The handle 106 itself is located along the line 202 such that if the handle 106 is positioned just above the start of the patella groove on the femur, the femoral wizard is approximately correctly placed. This line 202 is then orientated by dragging with the handle 110 so that the line 202 is moved onto the anterior femoral shaft proximal to the handle 106. Finally, the corner 112 between the lines 204 and 206 is manipulated so that the line 206 just contacts the distal and anterior margins of the condyles. The box formed by lines 202, 204, 205 and 206 then outlines the end of the femur. When the wizard 102A is correctly positioned, the line 203 represents the predicted surgical cut line and the parallel line 204 lies along the physiological bearing surface of the joint. Line 205, which is also parallel to line 203, is a measurement line that provides a geometrical parameter which is used to recommend an appropriately sized femoral component.

The ML view tibial wizard 104A comprises a tibial shaft axis definition line 118A having a drag handle 116 at each end, and an elongate rectangular box 120A also having a drag handles 121A and 121B at each end. The tibial shaft axis definition line 118A is at an angle to the long sides of the box 120A which is defined by a characteristic angle of the range of prostheses selected for consideration in the input step, known as the posterior slope angle. The ML view tibial wizard 104A is positioned by using the handles 116 to move the tibial shaft axis definition line 118A such that it is positioned along the axis of the tibia, by aligning it with the straight part of the posterior edge of the tibia. Then the handles 121A and 121B are used to drag the box 120A into position such that the line forming the upper long side of the box approximates to the knee joint line. FIG. 5 shows the ML view wizards 102A, 104A suitably positioned.

The user now refers to the AP X-ray image by clicking on a suitably-labelled button in the planning window to bring up this image in place of the ML X-ray image 200. In an alternative embodiment, the planning window may display both images at once.

Figure 6:
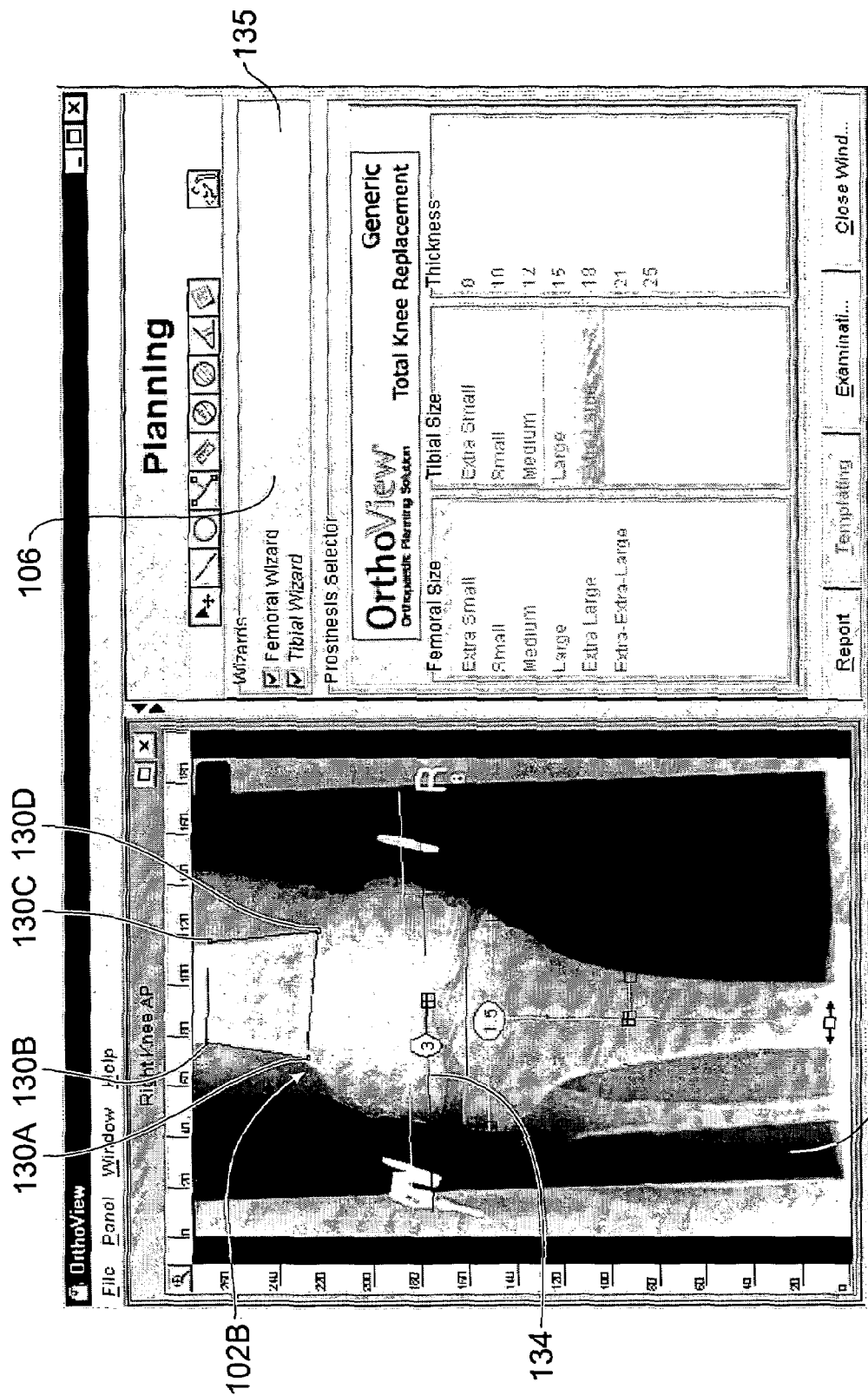
FIG. 6 shows a further screen shot of a computer window for performing a planning step of a second embodiment of the method of FIG. 1.
Figure 5A:
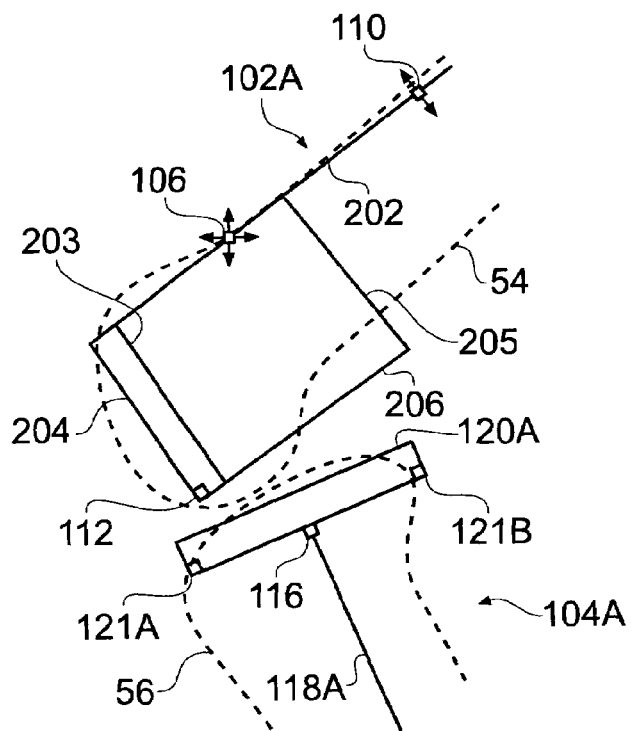
FIG. 5(a) shows a schematic representation of a geometrical construct used in the planning step of FIG. 5.

FIG. 6 shows a screen shot of the planning window with an AP X-ray image 210 displayed. Both the femoral and tibial wizards have been selected using the planning tool 106, so the AP view femoral wizard 102B and the AP view tibial wizard 104B are shown superimposed over the X-ray image 210.

Figure 6A:
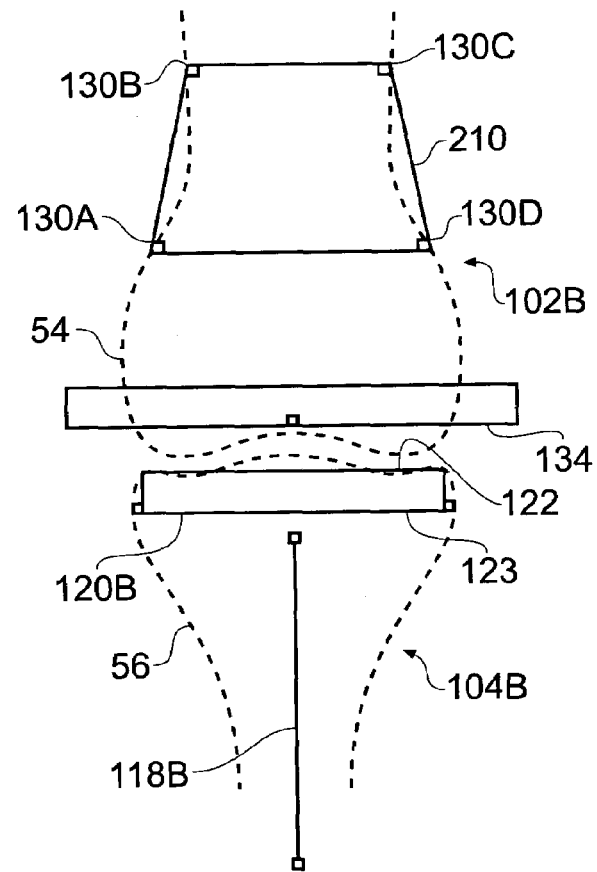
FIG. 6(a) shows a schematic representation of a geometrical construct used in the planning step of FIG. 6.

FIG. 6(a) shows the AP view femoral wizard 102B and tibial wizard 104B in more detail. An underlying image of a femur 54 and tibia 56 is shown in outline, with the wizards 102B, 104B in an approximate position. The AP view femoral wizard 102B comprises a quadrangular box 210 having a drag handle 130 at each corner, and a substantially horizontal elongate box 134 positioned below the box 210. The wizard 102B is positioned by dragging the handles 130 so as to outline the femoral shaft, so as to establish the axis of the femoral shaft, as shown in FIG. 6. This will give a femoral shaft centre line that will emerge either centrally in the intercondylar notch or slightly to one side. The box 134 is then positioned by the user so that its upper horizontal edge corresponds to the desired position of the distal femoral surgical cut line to be used in the forthcoming operation. Additionally, the user is required to enter into a dialogue box the valgus angle of the patient, which is determined in advance by physical examination of the patient (The valgus angle is the angle of displacement of the femur from the weight-bearing axis down the leg). This establishes the final parameter required for this wizard.

The AP view tibial wizard 104B comprises an elongate box 120B and a tibial shaft axis definition line 118B. As in the ML view tibial wizard, the angle between the box 120B and the line 118B is defined by the posterior slope angle of prostheses indicated for consideration in the input step. To position the AP view tibial wizard 104B, the user clicks on the tibial shaft axis definition line 118B and drags it over the tibia using the handles on either end to align it along the centre line of the tibial shaft. The user then positions the handles at either end of the elongate rectangular box 120B on the medial and lateral margins of the tibial plateau so that upper horizontal line 122 of the elongate rectangular box 120B is aligned with the physiological bearing surface line of the joint, or the lower horizontal line 123 of the elongate rectangular box 120B is aligned with the predicted surgical cut line. Clinical judgement and personal preference is used to determine which of these two lines 122 or 123 is used to appropriately position the AP view tibial wizard 104B. The distance between the two lines 122 and 123 is fixed and determined by the prosthetic system chosen by the user, because each system requires a surgical cut line to be made appropriately relative to the bearing surface of the joint. FIG. 6 shows the AP view femoral and tibial wizards 102B, 104B correctly positioned.

If desired, the user can move between the AP and ML images or can view both simultaneously to adjust the wizards until they are suitably positioned. As adjustments are made, a selection algorithm similar to that used in the first embodiment is executed to select suitable prostheses from a database, using parameters derived from the dimensions and positions of the manipulated wizards. The database is similar to that described for hip replacement prostheses, with the additional feature that each data file includes image data for two templates, one showing the ML outline of the prosthesis and one showing the AP outline. The results of the selection algorithm appear in information panels 135 in the planning window.

Once the user is satisfied with the positions of the wizards, the planning process can move onto the templating step, which is activated, as before, by the user clicking on a suitably labelled button in the planning window to move to a templating window.

Figure 7:
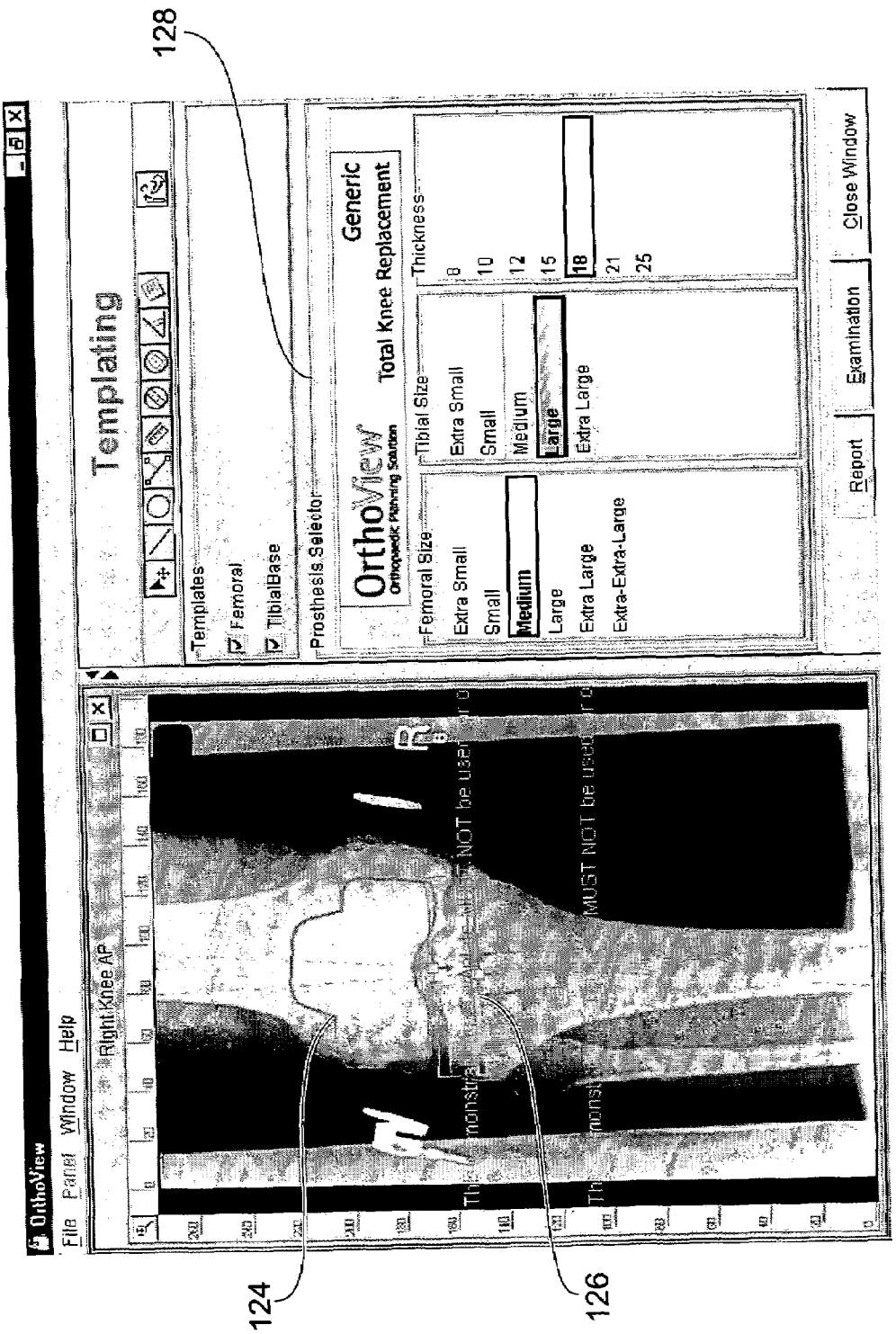
FIG. 7 shows a screen shot of a computer window for performing a templating step of a second embodiment of the method of FIG. 1.
Figure 8:
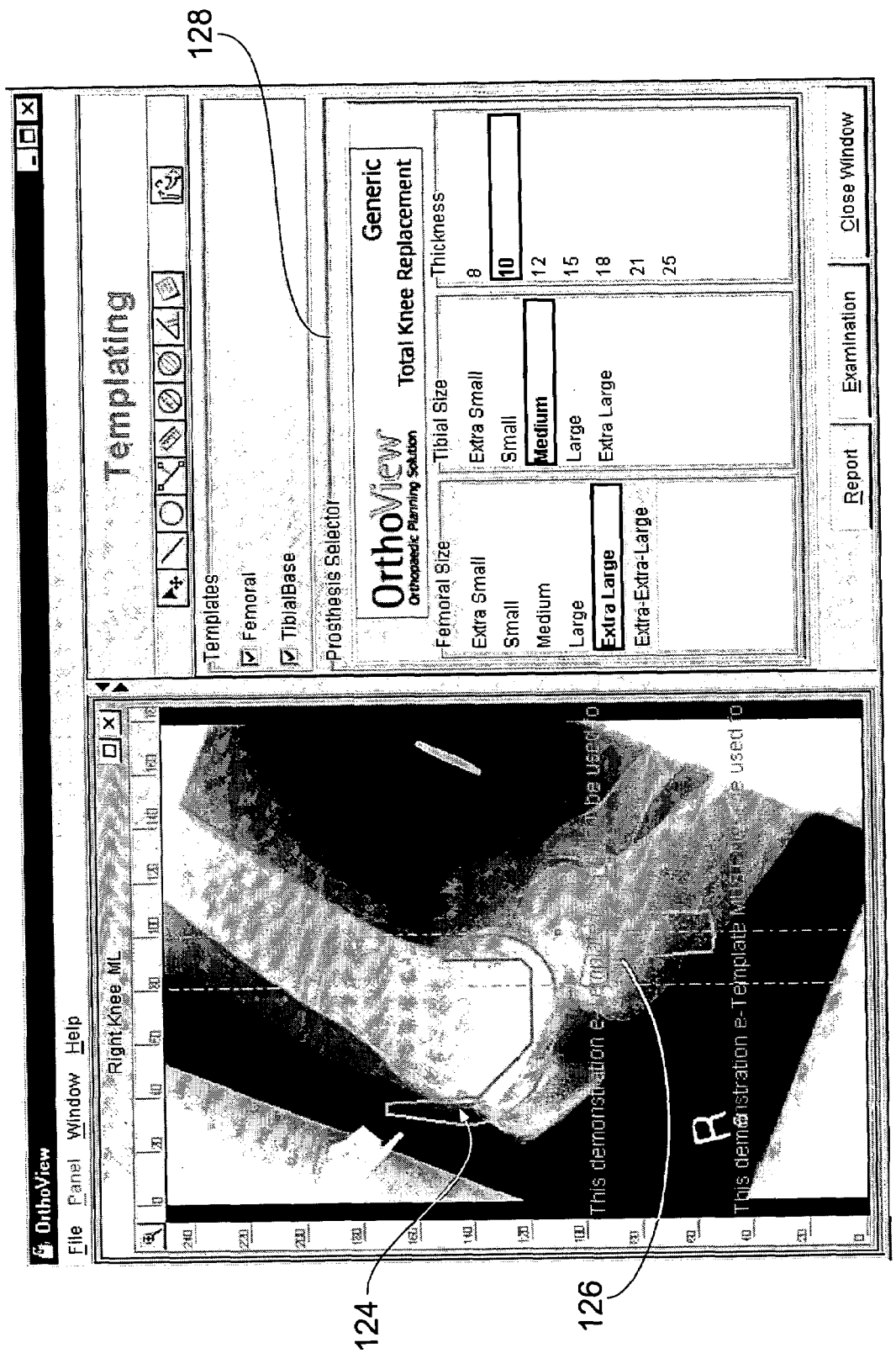
FIG. 8 shows a further screen shot of a computer window for performing a templating step of a second embodiment of the method of FIG. 1.

In the templating window, either of the two X-ray images can be displayed (or, alternatively, both can be displayed at one time). FIG. 7 shows a templating window displaying an ML image, and FIG. 8 shows a templating window displaying an AP image. In the templating window, the user is provided with chooser panels 128 listing values of parameters relevant to the two components of knee prostheses, with the results returned by the algorithm recommended by shaded areas. Choice of a parameter from each panel by the user allows the corresponding templates to be superimposed on the X-ray image for inspection by the user. The templates show femoral component 124 and the tibial component 126. These can be dragged across and rotated on the image independently so that the user can check the size and positioning before making a final choice of prosthesis.

Regarding the inter-relation between the wizards in the two views, this can be implemented in a various ways, and is based on the fact that the knee prosthesis components are three-dimensional, and bone measurements in three dimensions need to be considered to choose an appropriate prosthesis. Two possible implementations will now be described.

In the first implementation, the femoral wizard and the tibial wizard are each three-dimensional geometrical constructs, unrelated to each other. The AP and ML views of each wizard are two-dimensional projections of these constructs, so that in each view, each wizard appears as a two-dimensional collection of lines and shapes which are interconnected. Manipulation in one view hence moves corresponding parts of the three-dimensional construct so that the other projection in the other view is correspondingly altered. Thus the wizards can be manipulated in three dimensions and accurately matched to the imaged bone structure.

A second implementation uses two two-dimensional geometrical constructs for each of the tibial and femoral wizards, one construct for each view. In each view, the wizards can be manipulated, but there is no corresponding adjustment of that wizard in the other view. Each view therefore results in the determination of a different set of geometric parameters. The inter-relation is provided at the level of the database, where the data file for each prosthesis contains parameters describing that prosthesis. These parameters correspond to the geometric parameters determined from each of the two-dimensional wizards, so that each database entry is linked to both views of the wizard. Therefore, manipulation of the wizards in either view causes the selection algorithm to compare the geometric parameters with those in the database and possibly select and recommend a different prosthesis.

Further Embodiments

Although the present invention has been described in detail with respect to hip and total knee replacement surgery, it is not limited thereto. It can also be used for planning surgery for the replacement of other joints, including small joints and joints in the spine and upper limb, if a suitable database of prostheses is provided, and the geometrical constructs are modified so as to map the relevant measurements for the joint in question.

Although the first and second embodiments described herein use one and two patient images respectively, there is no limit to the amount of views which can be accommodated. However, the use of one or two images to plan orthopaedic surgery is typical, with three being used occasionally. To perform planning with the present invention using a particular number of images, a corresponding number of views of wizards must be provided (be they various two-dimensional projections of a single three-dimensional geometrical construct, or separate wizards linked via the parameters in the database), together with templates representing each of the appropriate outlines of the prostheses. Specifically, the present invention may be used for planning hip replacement surgery with ML patient images, if the database includes ML templates of the femoral and acetabular components, and a ML view hip wizard is provided. This is useful in planning hip revision surgery, which is performed in the event of failure of a previously implanted prosthestic hip joint. The replacement femoral component has a longer stem than the original. This means that a ML patient image is required to identify a well-fitting prosthesis because it is necessary to take account of a bend in the lower part of the femur in the ML plane.

What is claimed is:

1. A computer-implemented method of planning orthopaedic surgery, comprising:
   providing a library of templates representing orthopaedic prostheses;
   displaying a patient image showing anatomical features that are relevant for the orthopaedic surgery being planned;
   scaling the patient image according to user input;
   displaying over the patient image a geometrical construct comprising a plurality of interrelated shapes and lines defined by a plurality of interrelated geometric parameters corresponding to parameters describing the orthopaedic prostheses represented by the templates in the library;
   allowing a user to reconfigure the geometrical construct by adjusting the geometric parameters according to the anatomical features of the underlying patient image so as to specify a mapping of bone structure shown in the patient image; and
   automatically selecting at least one template from the library in accordance with the geometric parameters adjusted by the user.

2. The method of claim 1, wherein the patient image is an X-ray image.

3. The method of claim 1, wherein the geometric parameters include lengths and/or angles.

4. The method of claim 1, and further comprising, before automatically selecting:
   displaying a further patient image showing anatomical features that are relevant for the orthopaedic surgery being planned;
   scaling the further patient image according to user input;
   displaying over the further patient image a further geometrical construct defined by a plurality of interrelated further geometric parameters corresponding to parameters describing the orthopaedic prostheses represented by the templates in the library; and
   allowing a user to reconfigure the further geometrical construct by adjusting the further geometric parameters according to the anatomical features of the underlying further patient image so as to specify a mapping of bone structure shown in the further patient image;
   and wherein automatically selecting at least one template is in accordance with the geometric parameters and the further geometric parameters adjusted by the user.

5. The method of claim 4, wherein the patient image is an anterior-posterior view and the further patient image is a medio-lateral view.

6. The method of claim 1, wherein the geometric parameters are adjusted according to anatomical features of a femur so as to allow automatic selection of a template representing a femoral component of a hip prosthesis.

7. The method of claim 1, wherein the geometric parameters are adjusted according to anatomical features of a pelvis so as to allow automatic selection of a template representing an acetabular component of a hip prosthesis.

8. The method of claim 4, wherein the geometric parameters and the further geometric parameters are adjusted according to anatomical features of a knee joint so as to allow automatic selection of templates representing femoral and tibial components of a knee prosthesis.

9. A computer-implemented method of planning orthopaedic surgery, comprising:
   providing a library of templates representing orthopaedic implants;
   displaying first and second patient images showing anatomical features that are relevant for the orthopaedic surgery being planned;
   scaling the first and second patient images according to user input;
   displaying over the first patient image a first view of a geometrical construct, the geometrical construct comprising a plurality of interrelated shapes and lines being defined by a plurality of geometric parameters interrelated in three dimensions, the geometric parameters corresponding to parameters describing the orthopaedic prostheses represented by the templates in the library;

displaying over the second patient image a second view of the geometrical construct;

allowing a user to reconfigure the geometrical construct according to the anatomical features of the underlying patient images so as to specify a mapping of the bone structure shown in the first and second patient images, by adjusting geometric parameters adjustable in the first and second views; and automatically selecting at least one template from the library in accordance with the geometric parameters adjusted by the user.

10. The method of claim 9, wherein the first patient image is an anterior-posterior view and the second patient image is a medio-lateral view.

11. The method of claim 9, wherein the geometric parameters are adjusted according to anatomical features of a femur so as to allow automatic selection of a template representing a femoral component of a knee prosthesis.

12. The method of claim 9, wherein the geometric parameters are adjusted according to anatomical features of a tibia so as to allow automatic selection of a template representing a tibial component of a knee prosthesis.

13. The method of claim 9, wherein the geometric parameters are adjusted according to anatomical features of a femur so as to allow automatic selection of a template representing a femoral component of a hip prosthesis.

14. A computer-readable medium having stored thereon computer-readable instructions for implementing a method of planning orthopaedic surgery, comprising:

providing a library of templates representing orthopaedic prostheses;

displaying a patient image showing anatomical features that are relevant for the orthopaedic surgery being planned;

scaling the patient image according to user input;

displaying over the patient image a geometrical construct comprising a plurality of interrelated shapes and lines defined by a plurality of interrelated geometric parameters corresponding to parameters describing the orthopaedic prostheses represented by the templates in the library;

allowing a user to reconfigure the geometrical construct by adjusting the geometric parameters according to the anatomical features of the underlying patient image so as to specify a mapping of the bone structure shown in the patient image; and automatically selecting at least one template from the library in accordance with the geometric parameters adjusted by the user.

15. The computer-readable medium of claim 14, wherein the patient image is an X-ray image.

16. The computer-readable medium of claim 14, wherein the geometric parameters include lengths and/or angles.

17. The computer-readable medium of claim 14, and further comprising, before automatically selecting:

displaying a further patient image showing anatomical features that are relevant for the orthopaedic surgery being planned;

scaling the further patient image according to user input;

displaying over the further patient image a further geometrical construct defined by a plurality of interrelated further geometric parameters corresponding to parameters describing the orthopaedic prostheses represented by the templates in the library; and allowing a user to reconfigure the further geometrical construct by adjusting the further geometric parameters according to the anatomical features of the underlying further patient image so as to specify a mapping of the bone structure shown in the further patient image;

and wherein automatically selecting at least one template is in accordance with the geometric parameters and the further geometric parameters adjusted by the user.

18. The computer-readable medium of claim 17, wherein the patient image is an anterior-posterior view and the further patient image is a medio-lateral view.

19. The computer-readable medium of claim 14, wherein the geometric parameters are adjusted according to anatomical features of a femur so as to allow automatic selection of a template representing a femoral component of a hip prosthesis.

20. The computer-readable medium of claim 14, wherein the geometric parameters are adjusted according to anatomical features of a pelvis so as to allow automatic selection of a template representing an acetabular component of a hip prosthesis.

21. The computer-readable medium of claim 17, wherein the geometric parameters and the further geometric parameters are adjusted according to anatomical features of a knee joint so as to allow automatic selection of templates representing femoral and tibial components of a knee prosthesis.

22. A computer-readable medium having stored thereon computer-readable instructions for implementing a method of planning orthopaedic surgery, comprising:

providing a library of templates representing orthopaedic implants;

displaying first and second patient images showing anatomical features that are relevant for the orthopaedic surgery being planned;

scaling the first and second patient images according to user input;

displaying over the first patient image a first view of a geometrical construct, the geometrical construct comprising a plurality of interrelated shapes and lines being defined by a plurality of geometric parameters interrelated in three dimensions the geometric parameters corresponding to parameters describing the orthopaedic prostheses represented by the templates in the library;

displaying over the second patient image a second view of the geometrical construct;

allowing a user to reconfigure the geometrical construct according to the anatomical features of the underlying patient images so as to specify a mapping of the bone structure shown in the first and second patient images, by adjusting geometric parameters adjustable in the first and second views; and automatically selecting at least one template from the library in accordance with the geometric parameters adjusted by the user.

23. The computer-readable medium of claim 22, wherein the first patient image is an anterior-posterior view and the second patient image is a medio-lateral view.

24. The computer-readable medium of claim 22, wherein the geometric parameters are adjusted according to anatomical features of a femur so as to allow automatic selection of a template representing a femoral component of a knee prosthesis.

25. The computer-readable medium of claim 22, wherein the geometric parameters are adjusted according to anatomical features of a tibia so as to allow automatic selection of a template representing a tibial component of a knee prosthesis.

26. The computer-readable medium of claim 22, wherein the geometric parameters are adjusted according to anatomical features of a femur so as to allow automatic selection of a template representing a femoral component of a hip prosthesis.

27. The computer-readable medium of claim 14 or claim 22, wherein the computer-readable instructions are stored in a recording medium.

28. The computer-readable medium of claim 14 or claim 22, wherein the computer-readable instructions are conveyed on a transmission medium.

29. A computer system for implementing a method of planning orthopaedic surgery, comprising:
   memory in which is stored:
      a library of templates representing orthopaedic prostheses; and
      patient images showing anatomical features that are relevant for the orthopaedic surgery being planned;
   a display device operable to display one of the patient images; and
   a processor operable to:
      scale the displayed patient image according to user input;
      display over the patient image a geometrical construct comprising a plurality of interrelated shapes and lines defined by a plurality of interrelated geometric parameters corresponding to parameters describing the orthopaedic prostheses represented by the templates in the library;
      allow a user to reconfigure the geometrical construct by adjusting the geometric parameters according to the anatomical features of the displayed patient image so as to specify a mapping of the bone structure shown in the patient image; and
      automatically select at least one template from the library in accordance with the geometric parameters adjusted by the user.

30. The computer system of claim 29, wherein
   the display device is further operable to display a further one of the patient images; and
   the processor is further operable to:
      scale the displayed further patient image according to user input;
      display over the further patient image a further geometrical construct defined by a plurality of interrelated further geometric parameters, corresponding to parameters describing the orthopaedic prostheses represented by the templates in the library;
      allow a user to reconfigure the further geometrical construct by adjusting the further geometric parameters according to the anatomical features of the displayed further patient image so as to specify a mapping of the bone structure shown in the further patient image; and
      automatically select at least one template from the library in accordance with the geometric parameters and the further geometric parameters adjusted by the user.

31. A computer system for implementing a method of planning orthopaedic surgery, comprising:
   memory in which is stored:
      a library of templates representing orthopaedic prostheses; and
      patient images showing anatomical features that are relevant for the orthopaedic surgery being planned;
   a display device operable to display a first and a second of the patient images; and
   a processor operable to:
      scale the displayed patient images according to user input;
      display over the first patient image a first view of a geometrical construct, the geometrical construct comprising a plurality of interrelated shapes and lines being defined by a plurality of geometric parameters interrelated in three dimensions corresponding to parameters describing the orthopaedic prostheses represented by the templates in the library;
      display over the second patient image a second view of the geometrical construct;
      allow a user to reconfigure the geometrical construct according to the anatomical features of the underlying patient images so as to specify a mapping of the bone structure shown in the first and second patient images, by adjusting geometric parameters adjustable in the first and second views; and
      automatically select at least one template from the library in accordance with the geometric parameters adjusted by the user.

32. The computer system of claim 29 or claim 31, wherein the library of templates is stored such that it can be accessed by the processor via the Internet.

33. The computer system of claim 29 or claim 31, wherein the patient images are stored in an archive comprised within a Picture Archiving and Communication System.

* * * * *